US009986926B2

(12) United States Patent
Nelson et al.

(10) Patent No.: US 9,986,926 B2
(45) Date of Patent: Jun. 5, 2018

(54) Q-ONSET VENTRICULAR DEPOLARIZATION DETECTION IN THE PRESENCE OF A PACEMAKER

(75) Inventors: Alex T. Nelson, Portland, OR (US); Patricia A. Arand, McMinnville, OR (US); Marco Dalla Gasperina, Vancouver, WA (US)

(73) Assignee: Inovise Medical, Inc., Beaverton, OR (US)

( * ) Notice: Subject to any disclaimer, the term of this patent is extended or adjusted under 35 U.S.C. 154(b) by 1952 days.

(21) Appl. No.: 12/288,746

(22) Filed: Oct. 22, 2008

(65) Prior Publication Data

US 2009/0112108 A1 Apr. 30, 2009

Related U.S. Application Data

(60) Provisional application No. 61/000,615, filed on Oct. 26, 2007.

(51) Int. Cl.
*A61B 5/0402* (2006.01)
*A61B 7/02* (2006.01)
*A61B 5/0452* (2006.01)

(52) U.S. Cl.
CPC ............ *A61B 5/0402* (2013.01); *A61B 7/026* (2013.01); *A61B 5/0452* (2013.01)

(58) Field of Classification Search
CPC ... A61B 5/0452; A61B 5/0402; A61B 5/7217; A61B 5/7239; A61B 5/0472; A61B 5/7264; A61B 5/7275; A61N 1/08
USPC ................ 600/508–510, 513, 515–517, 519; 607/1–2, 9, 17, 25–27, 115, 116
See application file for complete search history.

(56) References Cited

U.S. PATENT DOCUMENTS

| | | | |
|---|---|---|---|
| 5,392,780 A | 2/1995 | Ogino et al. | |
| 5,758,654 A | 6/1998 | Burton-Krahn et al. | |
| 7,039,538 B2 | 5/2006 | Baker, Jr. | |
| 7,074,195 B2 | 7/2006 | Nelson et al. | |
| 7,096,060 B2 | 8/2006 | Arand et al. | |
| 7,096,064 B2 * | 8/2006 | Deno et al. ....................... | 607/9 |
| 7,113,820 B2 | 9/2006 | Schlegel et al. | |
| 7,171,269 B1 | 1/2007 | Addison et al. | |

(Continued)

FOREIGN PATENT DOCUMENTS

CA 1256507 6/1989

OTHER PUBLICATIONS

International Search Report, Serial No. PCT/US10/055696, dated Dec. 23, 2010, 13 pages total.

(Continued)

*Primary Examiner* — Deborah Malamud
(74) *Attorney, Agent, or Firm* — Kolisch Hartwell, P.C.

(57) ABSTRACT

A method utilizing computer processing for detecting, within a cardiac cycle, the earliest onset of global, Q-onset, ventricular depolarization in the presence of an operating pacemaker. The method, in general terms, features (a) gathering a plurality of ECG-obtained QRS heart-cycles waveforms, (b) identifying and categorizing of evidences and specific timings therein of intrinsic Q-onset and pacemaker spike events, (c) looking in a single, selected QRS waveform, between specific, defined first and second time marks, for the most significant slope change appearing in that waveform, and (d) designating to be the correct Q-onset that event which immediately precedes that slope change.

3 Claims, 2 Drawing Sheets

(56) References Cited

U.S. PATENT DOCUMENTS

| | | |
|---|---|---|
| 7,174,203 B2 | 2/2007 | Arand et al. |
| 7,225,021 B1 | 5/2007 | Park et al. |
| 7,248,923 B2 | 7/2007 | Maile et al. |
| 7,302,290 B2 | 11/2007 | Bauer |
| 7,424,321 B2 | 9/2008 | Wariar et al. |
| 7,435,221 B1 | 10/2008 | Bharmi et al. |
| 7,437,699 B2 | 10/2008 | Siejko et al. |
| 7,559,903 B2 | 7/2009 | Moussavi et al. |
| 7,819,814 B2 | 10/2010 | Gavriely et al. |
| 8,105,241 B2 | 1/2012 | Nelson et al. |
| 8,137,283 B2 | 3/2012 | Syeda-Mahmood et al. |
| 2002/0188329 A1 | 12/2002 | Struble |
| 2003/0187337 A1 | 10/2003 | Tarassenko et al. |
| 2004/0127792 A1 | 7/2004 | Siejko et al. |
| 2004/0230105 A1* | 11/2004 | Geva et al. .................. 600/301 |
| 2005/0027323 A1 | 2/2005 | Mulligan et al. |
| 2005/0080348 A1 | 4/2005 | Stahmann et al. |
| 2005/0222515 A1 | 10/2005 | Polyshchuk et al. |
| 2006/0079942 A1 | 4/2006 | Deno et al. |
| 2006/0155202 A1 | 7/2006 | Arand et al. |
| 2007/0038137 A1 | 2/2007 | Arand et al. |
| 2007/0055151 A1 | 3/2007 | Shertukde et al. |
| 2007/0191725 A1 | 8/2007 | Nelson |
| 2008/0021510 A1 | 1/2008 | Mi et al. |
| 2008/0125820 A1 | 5/2008 | Stahmann et al. |
| 2008/0177191 A1 | 7/2008 | Patangay et al. |
| 2008/0255465 A1 | 10/2008 | Nelson |
| 2009/0112108 A1 | 4/2009 | Nelson et al. |
| 2009/0165559 A1 | 7/2009 | Lec |
| 2010/0094148 A1 | 4/2010 | Bauer et al. |
| 2010/0331903 A1 | 12/2010 | Zhang et al. |
| 2012/0296228 A1 | 11/2012 | Zhang et al. |
| 2013/0030484 A1 | 1/2013 | Zhang et al. |

OTHER PUBLICATIONS

USPTO Office Action, U.S. Appl. No. 12/315,165, dated Nov. 12, 2010, 9 pages total.

USPTO Office Action, U.S. Appl. No. 11/264,328, dated May 9, 2008, 7 pages total.

USPTO Office Action, U.S. Appl. No. 11/264,328, dated Oct. 16, 2008, 8 pages total.

USPTO Office Action for U.S. Appl. No. 12/321,646 dated Jun. 17, 2011. 9pp.

USPTO Office Action for U.S. Appl. No. 12/288,712 dated Apr. 11, 2011. 5pp.

USPTO Office Action for U.S. Appl. No. 12/321,647 dated Jun. 1, 2011. 7pp.

USPTO Office Action for U.S. Appl. No. 12/321,650 dated Sep. 7, 2011. 8 pp.

USPTO Office Action for U.S. Appl. No. 12/005,555 dated Dec. 23, 2010. 7pp.

\* cited by examiner

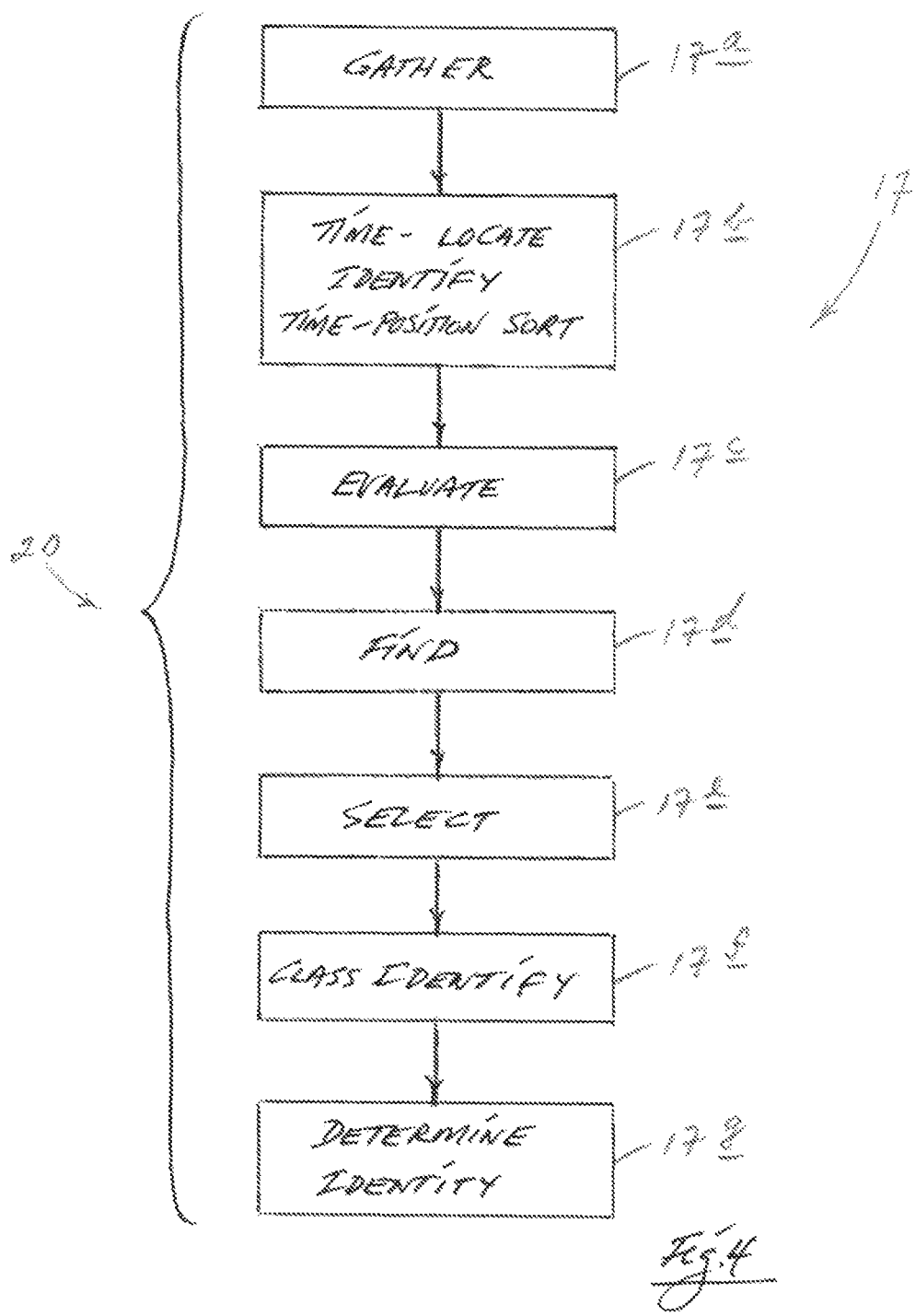

Q-ONSET VENTRICULAR DEPOLARIZATION DETECTION IN THE PRESENCE OF A PACEMAKER

CROSS REFERENCE TO RELATED APPLICATION

This application claims priority to the filing date, Oct. 26, 2007, of U.S. Provisional Patent Application Ser. No. 61/000,615, covering an invention entitled "Q-Onset Ventricular Depolarization Detection in the Presence of a Pacemaker". The entire disclosure content of that prior-filed provisional application is hereby incorporated herein by reference.

BACKGROUND AND SUMMARY OF THE INVENTION

In electrocardiography, the so-called QRS-onset, or Q-onset, in each cardiac-beat, or cardiac cycle, marks the start of electrical depolarization of the heart ventricles. In the context of correlated electroacoustic cardiography, this well-recognized QRS-onset (or Q-onset, a term which is used herein interchangeably with QRS-onset) fiducial is important as a reference for computing the respective durations of a number of important heart-functionality time intervals, such as the electromechanical activation time interval (EMAT) between Q-onset and the closure of the mitral valve. In fact, and as those skilled in the art well know, one of the most important measurements which is relied upon in terms of assessing a person's heart functionality is this EMAT time interval, also referred to as the QS1 time interval—the time interval between Q-onset and the occurrence of the first heart sound (S1). Accordingly, accurate determination of the time of Q-onset in each cardiac cycle is extremely critical to heart-behavior assessment.

In circumstances where a pacemaker is in place in a subject, Q-onset presence and timing confusion can occur. For example, if a particular cardiac cycle is in fact initiated by a ventricular pacemaker impulse, referred to as a pacer spike, rather than by an intrinsic (anatomical) Q-onset event, then the onset of depolarization is best represented by the occurrence time of such a pacer spike. Knowing what is the truth about the time-initiation of depolarization onset is, of course, mandatory for achieving measurement accuracy based upon this initiation event, and so it is very important to distinguish these two different kinds of depolarization-initiation events so as to identify clearly what event to select as the one representing true Q-onset. Put another way, and as those skilled in the art well recognize, where a pacemaker is present, one cannot simply rely on pacemaker-activity output to describe, with confident accuracy, the reality of Q-onset, because of the fact that the relevant pacemaker (a) may be out of synchronization, (b) may possibly be an atrial rather than a ventricular pacemaker, and (c) if it is a bi-ventricular pacemaker, there must be some way of identifying which heart chamber is specifically associated with pacemaker activity.

In this setting, accordingly, the present invention is concerned particularly with identifying, with as much accuracy as possible, the time, during each heartbeat, of true Q-onset. In a more particular sense, the present invention is concerned with clearly identifying this Q-onset event in a circumstance where a subject is equipped with a pacemaker whose pacing pulses may (but not necessarily so) be the true indicators of Q-onset.

In relation to the preferred and best-mode manner of practicing the present invention, which includes algorithmically programmed computer processing, there are several categories of ECG and pacemaker information which are especially relevant. These categories define the key pieces of input information which, for a selected, predetermined time span (such as about 10-seconds), which includes a number—a collection—of successive cardiac cycles, are gathered/obtained and supplied to what is referred to herein as a Q-Onset Selection block which, essentially, takes the form of at least a portion of an appropriately algorithmically programmed digital computer that forms one of the central operational systemic "components" of the invention. It is by the operation of this block that an accurate assessment of Q-onset is made.

Such input information supplied to this block preferably includes conventional, multi-lead (such as 12-lead, though a lesser number of leads may be employed if desired) ECG information which also carries accompanying information defining, for each cardiac cycle in the collection of the mentioned number of gathered, successive cardiac cycles, the time locations of conventionally detected (intrinsic) Q-onset events and of pacemaker spike events. Another piece of input information is derived directly from a selected, single ECG lead, such as the so-called V-4 ECG lead. Also supplied to the Q-Onset Selection block is information specifically relevant to pacemaker, or pacer, operation, derived synchronously from the just-mentioned, conventionally acquired ECG information. This pacemaker-operation information specifically includes pacer spike information in terms of the time occurrences of pacer spikes, as well as their types, i.e., as being either atrial, ventricular, first bi-ventricular, or second bi-ventricular, and more broadly speaking as being either ventricular or bi-ventricular.

Still a further piece of information which is relevant, and which may be supplied by the same equipment and methodology which supplies the mentioned, conventionally acquired ECG information, is a characterization of the types of heartbeats, or cardiac cycles, which have been detected during the above-mentioned, predetermined time span. In this regard, there are recognized, for the purpose of the description of the present invention, to be two, different, so-called cardiac cycle types, one of which is referred to as being an intrinsically, or internally (i.e., by the anatomy), initiated cardiac cycle, and the other of which is referred to as being a pacer-spike-initiated cardiac cycle.

With such input information, the Q-onset selection activity of the invention functions to produce, among other things as reportable output information, the relevant, confirmation, Q-onset timing and identity output information. This output information fundamentally, and variously, defines, for each cardiac cycle involved in an investigation, (a) the times within these cycles of "best-determined" Q-onset, (b) the identifying class (per cycle) of the associated, selected, Q-onset event as being either an intrinsic event or a pacer event, and (c) the associated cycle class-identity (intrinsic or pacer).

In general terms, such Q-onset selection, per cardiac cycle, uniquely involves (1) during a predetermined time span which includes a plurality of successive, QRS cardiac cycles, gathering both ECG and pacemaker-spike information for, and within, each such cycle, (2) with respect to each such gathered cardiac cycle, time-locating, identifying and time-position sorting, first to last, each intrinsic Q-onset and each pacemaker-spike event, including specifically identifying each pacemaker-spike event as being one of ventricular or bi-ventricular, (3) also with regard to each such cardiac cycle, evaluating, with respect a single, selected, QRS waveform, the waveform slope therein from (a) a time just preceding, to (b) a time just following, the mentioned, time-position sorted, first-in-time and last-in-time one of such time-located, identified and sorted events, respectively, (4) from the mentioned slope evaluating practice, finding the time, in the mentioned, single, selected QRS-waveform, of the first substantial QRS-waveform slope change, (5) in each cardiac cycle, selecting to be the correct Q-onset therein the time-sorted event in that cycle whose time position most immediately precedes the time of the mentioned, found, first-substantial slope change, and (6) with respect to each cardiac cycle, maintaining the identity of the selected to-be-correct Q-onset event.

Such Q-onset determination is followed, among other things, by appropriate presenting and/or reporting of the determination outcome so as to enable thereafter, and as an illustration of special utility, accurate calculation of the kinds of important heart-functionality time intervals, like the EMAT interval mentioned earlier herein.

These and other features, advantages and reportable Q-onset outcomes which are offered by the present invention will become more fully apparent as the detailed description of the invention which follows below is read in conjunction with the accompanying drawings. This detailed invention description is specifically presented in block/schematic structural and methodologic drawings, and in text terminology, both very familiar to those generally skilled in the relevant art. Accordingly, unnecessary details that define medical terminology are not included herein. Also not specifically included are lines/details of computer-programming code which may conventionally be employed by ones skilled in the programming art to implement the two algorithms which are set forth herein in very understandable, high-level, algorithmic terminology and architecture.

DESCRIPTION OF THE DRAWINGS

FIG. 2 specifically shows practice of the invention employing a pacemaker (pacer) spike detector and a pacemaker (pacer) spike classifier for providing pacemaker spike information relevant to Q-onset detection and identification.

FIG. 4 illustrates, in simplified, schematic, word-labeled and flow-connected block-diagram form, the methodologic processing steps of the invention.

DETAILED DESCRIPTION OF THE INVENTION

Figure 1:
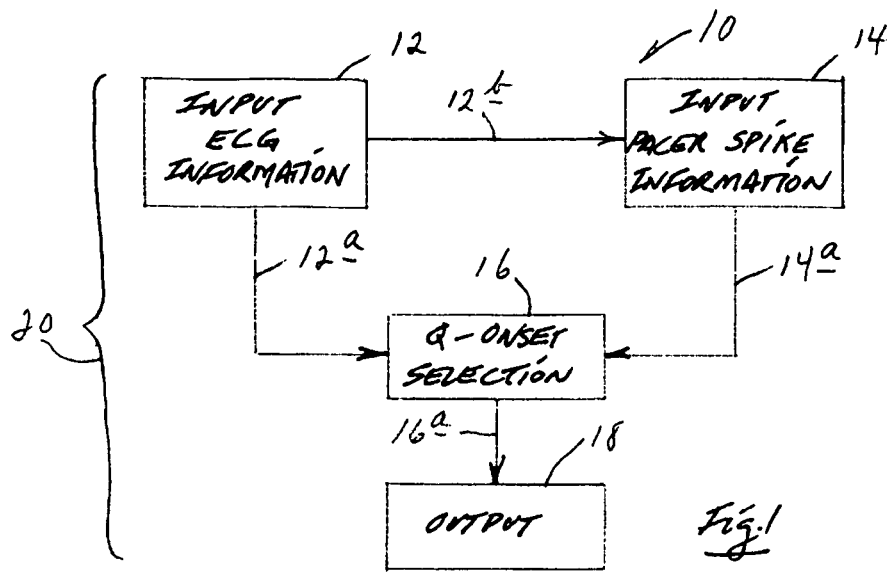
FIG. 1 is a high-level, block/schematic diagram generally illustrating the preferred and best-mode embodiment of, and the manner of practicing, the methodology of the present invention.

Turning now to the drawings, and referring first of all to FIG. 1, here, illustrated generally at 10, and including four, "high-level" blocks 12 (Input ECG Information), 14 (Input Pacer Spike Information), 16 (Q-Onset Selection), 18 (Output) is a broad, overview illustration of the preferred and best-mode embodiment of, and manner of practicing, the present invention. A lateral bracket 20 in this figure represents the presence and utilization of a suitably programmed digital computer which performs all required data processing in the practice of the invention. More will be said about this computer, and its operation, shortly.

Block 12 represents the action of conventional ECG-lead collection, and thereafter the inputting from block 12 to block 16, via a data-flow connection 12a, of the several kinds of relevant ECG information mentioned above herein, as well as certain, relevant pacemaker (pacer) spike information which is naturally acquired over the employed ECG leads. Block 14 represents the gathering from block 12, over a data-flow connection 12b, and the inputting, via a data-flow connection 14a also to block 16, of similar, relevant pacemaker spike information, as generally mentioned earlier herein, derived from block 12. To the extent that data processing is, or may be, required in the handling of the flow of information within, and from, blocks 12, 14, computer 20 takes care of these tasks.

Information provided over connections 12a, 14a by blocks 12, 14, respectively, to block 16, wherein Q-Onset Selection takes place in accordance with practice of the present invention, is appropriately computer processed by computer 20 within the environment of block 16 utilizing a unique algorithm identified herein (and described architecturally in instructive detail below) as Algorithm I. Such information processing within block 16 results, as will shortly be explained, and through a block 16 to block 18 data-flow connection 16a, in the supply, to and via Output block 18, of accurately determined Q-onset timing information, as well as Q-onset type classification/identification, and certain other pieces of important information for, and in relation to, each of the earlier mentioned, selected-time-span number of successive cardiac cycles. In this regard, it should be understood that the illustrative selection of ten-seconds for a useful, predetermined time span is not a required, or "magic", time-span number. Any appropriate, predetermined time span may be chosen, though ten-seconds for such a span has proven to be entirely satisfactory.

From the computer-processed information presented as output information by Output block 18, accurate Q-onset, and certain other, valuable information is made available for all subsequent purposes, such as for calculating the time durations of various important heart-functionality parameters, like the previously mentioned EMAT parameter.

Figure 2:
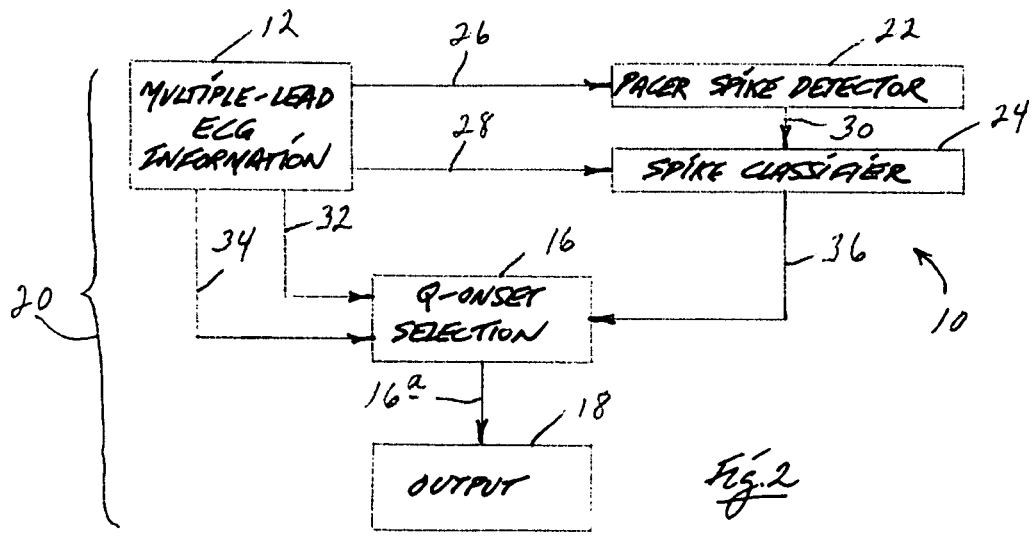
FIG. 2 is a more elaborated, block/schematic diagram illustrating in somewhat greater detail that which is pictured more generally in FIG. 1.

Turning attention now to FIG. 2, as can be seen, several of the blocks which appear in this figure are the same as several, like blocks which appear in just-described FIG. 1. More specifically, previously mentioned blocks 12, 16, 18 appear in FIG. 2, along with two additional blocks 22, 24. Also appearing similarly in FIG. 2 is lateral bracket 20 representing the previously mentioned, algorithmically programmed digital computer which furnishes all data processing required in accordance with practice of the invention.

Block 22 takes the form of a conventional pacer spike detector. Block 24 takes the form of a unique, computer-20-implemented pacer spike classifier which is constructed, and which performs, in accordance with a unique algorithm, described below as Algorithm II, created and operational in accordance with features of the present invention. Blocks 22, 24 collectively function as previously mentioned block 14 which appears in FIG. 1.

As will be mentioned further, computer 20 implements Algorithms I and II, and the operations and behaviors of blocks 16, 24, respectively, will shortly be described in the contexts of these two algorithms.

Completing a description of what is shown specifically in FIG. 2, several additional data-flow connections are shown variously interconnecting the several blocks pictured in this figure. In particular, a data-flow connection 26 carrying multiple-lead ECG information connects block 12 to the pacer spike detector. A data-flow connection 28, carrying the same ECG information, connects block 12 with the pacer spike classifier. Connections 26, 28 collectively make up previously described data-flow connection 12b. A data-flow connection 30 supplies information from the pacer spike detector to the pacer spike classifier.

From block 12, a data-flow connection 32 provides Q-Onset Selection block 16 with multi-lead ECG information, and a data-flow connection 34 supplies, from block 12 to Q-Onset Selection block 16, single-ECG-lead V4 ECG information. The information supplied over connection 32 includes, for each of the previously mentioned, successive cardiac cycles, the perceived times of intrinsic Q-onset and pacer spike events present during those cycles. Connections 32, 34 collectively make up previously mentioned data-flow connection 12a.

Extending from the pacer spike classifier 24 is a data-flow connection 36 which is the same as previously described data-flow connection 14a, and which supplies, from the classifier to Q-Onset Selection block 16, pacer spike times and classifications detected and processed by blocks 22, 24 during the predetermined time span of cardiac-cycle gathering. As was mentioned earlier, the manner of operation of classifier 24 in accordance with Algorithm II will be explained shortly.

Within the control of block 16, in cooperation with blocks 12, 22 and 24, under the operation of digital computer 20, and under circumstances wherein information, as generally described above, is supplied to block 16 via connections 32, 34, 36, which information has been gathered and processed by blocks 12, 22, 24 over the period of time embracing the above-mentioned gathering of successive cardiac cycles, Q-onset determination/selection is performed in accordance with the following Algorithm I.

Algorithm I

1. With respect to each gathered cardiac cycle, time-locate, identify and time-position sort, first to last, each intrinsic Q-onset, and each pacemaker-spike, event, including specifically identifying each pacemaker-spike event as being one of ventricular or bi-ventricular;
2. Also with regard to each such cardiac cycle, evaluate, with respect a single, selected, QRS waveform, the waveform slope therein from (a) a time just preceding, to (b) a time just following, the mentioned, time-position sorted, first-in-time and last-in-time one of such time-located, identified and sorted events, respectively;
3. Based on such slope evaluating, find the time, in the mentioned, single, selected QRS-waveform, of the first substantial QRS-waveform slope change;
4. In each cardiac cycle, select to be the correct Q-onset therein the time-sorted event in that cycle whose time position most immediately precedes the time of the mentioned, found, first-substantial slope change, and
5. With respect to each cardiac cycle, maintain the identity of the selected-to-be-correct Q-onset event.

In the preferred implementation of Algorithm I by computer-20 processing, slope evaluating is performed by the computer effectively using a line having a length of about 14-milliseconds in duration as a projection on the QRS-waveform time axis of the subject, single, selected QRS-waveform wherein slope is being evaluated, (a) with both ends of this line lying on that waveform, (b) by moving the line from a first time which is just before the above-mentioned, first-in-time, time-sorted event, to a second time, which is just after the above-mentioned, last-in-time, time-sorted event, and (c) by noting the magnitude of the slope in existence at points distributed on the subject waveform between these just-stated first and second times. In this slope-evaluating practice, the single, selected waveform employed for this purpose is that which comes from the V4 ECG lead via connection 34.

In the invention practice illustrated in FIG. 2, pacer spike information delivered to block 16 over connection 36 from the pacer spike classifier is developed in the classifier in accordance with the implementation by computer 20 of what has been referred to above as being Algorithm II.

The steps of this algorithm, expressed in terms well understood by those skilled in the relevant art, and performed in relation to the totality of the successive cardiac cycles gathered during the predetermined time span, are as follows.

Algorithm II

1. Compute the "forward difference" time intervals between each pacer spike in the preceding, two pacer spikes;
2. Compute the "backward difference" time intervals between each pacer spike and the subsequent, two pacer spikes;
3. Associate each pacer spike with the cycle having the most proximal QRS-onset time;
4. Compute the "Q. difference" as the time interval between each pacer-spike time and the QRS-onset time of the associated cycle;
5. For each pacer spike time, compute three similarity scores against each of the other pacer times as
   (a) the absolute difference between the forward differences,
   (b) the absolute difference between the backward differences, and
   (c) the absolute difference between the Q. difference;
6. Combine the three similarity scores as appropriate, taking into account the validity of each;
7. Group with each pacer spike all other pacer spikes having a similarity score below a predetermined threshold;
8. Allow only one pacer spike per cycle to be in each pacer-spike group, discarding duplicates;
9. Allow only three pacers spikes to be associated with each cycle;
10. For each cycle, assign each pacer spike to the appropriate type (atrial, ventricular, bi ventricular) based on its timing relative to QRS-onset and the presence of other pacers spikes in that cycle;
11. Ensure that all pacer spikes in a group have the same type by looking across all cycles;
12. Check for consistency of timing relative to QRS-onset of pacer spikes of the same type;
13. Require biventricular pacer spikes to come in pairs, discarding the ones that are not paired; and
14. Report the times, types, and cycle associations of the valid pacer spikes.

Following implementation of both algorithms in the full practice of the invention, output information is reported/ presented, etc., by block 18. This output information preferably includes, for each cardiac cycle involved in a plural-cycle investigation seeking Q-onset as described above, (a) the times within the plural cycles of "best-determined" Q-onset, (b) the identifying class (per cycle) of the associated, selected, Q-onset event as being either an intrinsic event or a pacer event, and (c) the associated cycle class-identity (intrinsic or pacer). The output information made available by practice of the invention is highly accurate in terms of the key task of reliably identifying "real" Q-onset notwithstanding the possible confusing presence of a pacemaker, and therefore sets the stage for reliable and accurate determinations of various, Q-onset-dependent, heart-functionality time-duration parameters, such as the earlier-mentioned, important EMAT parameter.

Figure 3:
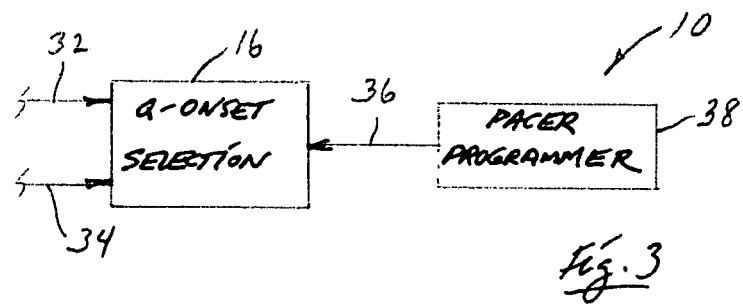
FIG. 3 is a fragmentary, block/schematic diagram describing one modified form of the invention. This figure shows practice of the invention wherein pacemaker information is supplied by a conventional pacemaker (pacer) programmer device.

Focusing attention now on the fragmentary illustration presented in FIG. 3, here the structure and methodology 10 of the present invention are illustrated in a modified form. Pacer spike "detection" and classification information is supplied to block 16 via connection 36 from a conventional pacer programmer which is represented by a block 38 in this figure. Except for the fact that here this pacer spike detection and classification information is supplied differently from the manner in which it is supplied in accordance with the illustration seen in FIG. 2, in all other respects, the operation of the methodology of the invention is identical, in terms of computer-20 implementation of Algorithms I, II to the gathered and processed ECG and pacer spike data.

Directing attention to FIG. 4, here there are schematically illustrated at 17 the key steps that are performed during practice of the methodology of the present invention. The large bracket designated with reference numeral 20 appearing at the left side in this figure is employed to indicate that what is shown to the right of this bracket essentially furnishes method-step detailing of what is shown at 20, from different perspectives, in FIGS. 1 and 2.

As can be seen, FIG. 4 includes, generally designated at 17, seven, process-flow-connected blocks which are marked 17a-17g, inclusive. These blocks are individually, in high-level, simplified forms, word-labeled to indicate (in abbreviated fashions) all of the principal steps of the invention. FIG. 4 also clearly illustrates these steps' overall, collaborative arrangement and cooperative organization—i.e., the "architecture" of applicants' claimed methodology.

Presented now immediately below is a methodologic description of the practice of the present invention, as such practice is illustrated in the flow of processing which takes place progressing downwardly in FIG. 4 through, as will be explained, some, or alternatively all, of these seven blocks. FIG. 4 thus affords three, different-perspective views of the present invention, each of these three views depending upon which specific blocks are considered to be in functional collaboration with one another.

In this context, one manner of visualizing the invention involves focusing on just what occurs within the cooperative actions that take place within blocks 17a-17e, inclusive. Another manner of considering the invention methodology involves adding to the performances of blocks 17a-17e, inclusive, what occurs within block 17f. Still a further way of viewing the methodology of the invention is to consider the performances contributed by all seven of the illustrated blocks.

In block 17a, during a predetermined time span which is chosen to include a plurality of successive, QRS cardiac cycles, both ECG and pacemaker-spike information contained in each of these cycles is gathered.

Block 17b, for each cardiac cycle wherein information of the categories just mentioned in relation to block 17a is gathered, performs (a) time-locating, (b) identifying, and (c) time-position sorting, first-to-last, of each existing intrinsic Q-onset event and each existing pacemaker-spike event. Additionally, block 17b specifically identifies each pacemaker-spike event as being one of either ventricular or bi-ventricular.

Coupled methodologically as shown to block 17b, and for each cardiac cycle dealt with by block 17b, block 17c next performs the steps of evaluating the QRS waveform slope in each such cycle from a time just preceding to a time just following the time-position-sorted, first-in-time and last-in-time one of the time-located, identified and sorted events resulting from the performance of and in block 17b.

Based upon the slope evaluating which takes place in block 17c for each cardiac cycle, block 17d, performs the task of finding the time, in each such cycle, of the first, substantial QRS-waveform slope change.

Block 17e, in cooperation with what takes place in block 17d, then selects to be the correct, earliest onset of ventricular depolarization in each cardiac cycle the time-sorted event in that cycle whose time position most immediately precedes the time of the found, first, substantial slope change found by the operation of block 17d.

From the operation performed in block 17e, block 17f, for each cardiac cycle, identifies the class of the associated, selected-to-be-correct, earliest onset of ventricular depolarization event as being one of either an intrinsic event or a pacer event, and gives to the associated cycle a cycle class-identity which is related to that of the associated, selected-to-be correct earliest onset of ventricular polarization.

Finally, methodology block 17g, which is processing-flow connected as shown to methodology block 17f, performs the further step involving, across all cardiac cycles which are associated with the mentioned predetermined time span having the same class-identity, determining the dominant identity of the selected earliest onset of ventricular depolarization event as being one only of intrinsic, ventricular and bi-ventricular, and based upon such determining, forces all cycles in a given class of cycles also to have the same event identity.

Accordingly, a unique and highly accurate methodology for determining Q-onset in the presence of an operating pacemaker has been illustrated and described herein, in preferred and best-mode, and in modified, forms. And, while this is so, we recognize that a number of variations and modifications may be perceived and implemented by those generally skilled in the relevant art without departing from the scope and spirit of the invention.

We claim:
1. A method employable in the presence of an operating pacemaker for determining the true onset of ventricular depolarization in a subject's cardiac cycles comprising
during a selected, predetermined time span which includes a plurality of the subject's cardiac cycles, acquiring, externally, EGC waveform data reflected in those cycles,
gathering, solely from within such acquired data, and with respect to each included cardiac cycle represented in that data, electrical-event waveform information respecting the two, potential, true-onset event candidates—QRS-intrinsic, and pacemaker-non-intrinsic, and, in relation to the gathered, QRS-intrinsic and pacemaker-non-intrinsic, electrical event waveform information, for each cycle in the mentioned plurality of cycles, and utilizing an appropriately programmed computer, identifying which of the QRS-intrinsic and pacemaker-non-intrinsic events present in the cycle is to be determined as being the one reflecting true ventricular-depolarization onset through
 (a) time-locating, time-position-sorting, and identifying as first-in-time and last-in-time, the respective events in the cycle of a QRS-intrinsic event and of a pacemaker-non-intrinsic event, and identifying, further, each pacemaker-non-intrinsic event as being one of ventricular or bi-ventricular,
 (b) evaluating, in the gathered waveform information associated with the cycle, the waveform slope therein from a time just preceding the identified first-in-time event to a time just following the identified last-in-time event,
 (c) based on said evaluating, finding the time of the first substantial waveform slope change, and
 (d) selecting to be the correct event in the cycle which reflects true ventricular depolarization onset the time-position-sorted event whose time position in the cycle most immediately precedes the time of the found, first-substantial slope change.

2. The method of claim 1 which further comprises giving to each selected-to-be-correct, true onset of ventricular depolarization event a class identity with the name of either intrinsic or non-intrinsic, as appropriate, and applying to the associated cardiac cycle a cycle class-identity which has the same name.

3. The method of claim 2 which further comprises, across all cycles included in the predetermined time span having the same class-identity, determining the dominant identity of the selected true onset of ventricular depolarization event as being one only of intrinsic, non-intrinsic ventricular, and non-intrinsic bi-ventricular, and forcing all cycles in a given class of cycles also to have the same event identity.

* * * * *